(12) United States Patent
Jain et al.

(10) Patent No.: US 11,051,773 B2
(45) Date of Patent: Jul. 6, 2021

(54) SYSTEMS AND METHODS FOR IMAGING WITH IMPROVED DOSAGES

(71) Applicant: General Electric Company, Schenectady, NY (US)

(72) Inventors: Nitin Jain, Bangalore (IN); Charles Stearns, Waukesha, WI (US); Savitha V S, Bangalore (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 698 days.

(21) Appl. No.: 15/830,619

(22) Filed: Dec. 4, 2017

(65) Prior Publication Data
US 2019/0167213 A1 Jun. 6, 2019

(51) Int. Cl.
*A61B 6/00* (2006.01)
*A61B 6/03* (2006.01)
*G06T 11/00* (2006.01)

(52) U.S. Cl.
CPC ............ *A61B 6/4057* (2013.01); *A61B 6/032* (2013.01); *A61B 6/037* (2013.01); *A61B 6/5235* (2013.01); *A61B 6/5258* (2013.01); *A61B 6/544* (2013.01); *A61B 6/582* (2013.01); *G06T 11/005* (2013.01); *G06T 2210/41* (2013.01)

(58) Field of Classification Search
CPC ....... A61B 6/032; A61B 6/037; A61B 6/4057; A61B 6/5235; A61B 6/5258; A61B 6/544; A61B 6/582; G06T 11/005; G06T 2210/41
See application file for complete search history.

(56) References Cited

U.S. PATENT DOCUMENTS

| 7,851,763 B2 | 12/2010 | Bendriem et al. |
| 2006/0097175 A1* | 5/2006 | Ganin ............... G01T 1/1611 250/363.03 |
| 2008/0242915 A1* | 10/2008 | Jackson ............... G21H 5/02 600/4 |
| 2013/0079581 A1* | 3/2013 | Agamaite ............ A61N 5/1064 600/4 |
| 2018/0289340 A1* | 10/2018 | Trindade Rodrigues ............... A61B 6/56 |

OTHER PUBLICATIONS

Charles W. Stearns; "Estimating an Acquisition-Specific NEC Curve for PET Acquisitions", Nuclear Science Symposium Conference Record, IEEE, 2003.

(Continued)

*Primary Examiner* — Amelie R Davis
(74) *Attorney, Agent, or Firm* — The Small Patent Law Group LLC; Dean D. Small

(57) ABSTRACT

A system is provided that includes at least one detector and a processing unit. The at least one detector is configured to acquire imaging information. The processing unit is operably coupled to the at least one detector, and is configured to acquire the imaging information from the at least one detector. The processing unit is configured to acquire patient scanning information for an imaging operation, determine a target activity based on the patient scanning information, determine a target time for performing the imaging operation corresponding to the target activity, perform the imaging operation at the target time to acquire targeted imaging information; and reconstruct an image using the targeted imaging information.

16 Claims, 7 Drawing Sheets

(56) References Cited

OTHER PUBLICATIONS

M. Danna, M. Lecchi, V. Bettinardi, M. C. Gilardi, C. W. Stearns, G. Lucignani, and F. Fazio; "Generation of the Acquisition-Specific NEC (AS-NEC) Curves to Optimize the Injected Dose in 3D 18F-FDG Whole Body PET Studies", IEEE Transactions on Nuclear Science, vol. 53, No. 1, Feb. 2006.

\* cited by examiner

SYSTEMS AND METHODS FOR IMAGING WITH IMPROVED DOSAGES

BACKGROUND OF THE INVENTION

The subject matter disclosed herein relates generally to apparatus and methods for diagnostic medical imaging, such as, for example, positron emission tomography (PET) imaging and/or computed tomography (CT) imaging.

PET is a medical imaging technique that provides functional information regarding physiological processes of an object (e.g., human patient) being imaged. Radiopharmaceuticals may be administered to a patient, resulting in emitted positrons, which undergo annihilation with electrons, generating photons that travel in opposite directions. The photons may be detected, with each event stored in an array referred to as a sinogram. The measured sinogram data may be used to reconstruct a three-dimensional distribution corresponding to the radiopharmaceutical as part of an image reconstruction.

As the radiopharmaceutical decays, the activity level of the radiopharmaceutical changes. Image quality may suffer when an imaging scan is performed at an activity level of the radiopharmaceutical that differs from an ideal, optimal, or preferred value or range.

BRIEF DESCRIPTION OF THE INVENTION

In one embodiment, a system is provided that includes at least one detector and a processing unit. The at least one detector is configured to acquire imaging information. The processing unit is operably coupled to the at least one detector, and is configured to acquire the imaging information from the at least one detector. The processing unit is configured to acquire patient scanning information for an imaging operation, determine a target activity based on the patient scanning information, determine a target time for performing the imaging operation corresponding to (e.g., based on) the target activity, perform the imaging operation at the target time to acquire targeted imaging information; and reconstruct an image using the targeted imaging information.

In another embodiment, a method is provided that includes acquiring, with at least one processor, patient scanning information for an imaging operation. The method also includes determining, with the at least one processor, a target activity based on the patient scanning information. Also, the method includes determining a target time for performing the imaging operation corresponding to (e.g., based on) the target activity. Further, the method includes performing the imaging operation at the target time to acquire targeted imaging information. The method also includes reconstructing an image using the targeted imaging information.

In another embodiment, a method is provided that includes acquiring a series of images across a population of patients. The method also includes correlating each image with scanning information corresponding to the image. Further, the method includes determining a corresponding activity level for a peak noise equivalent count (NEC) for each image. The method also includes developing a model based on the corresponding NEC for each of the images.

DETAILED DESCRIPTION OF THE INVENTION

Figure 1:
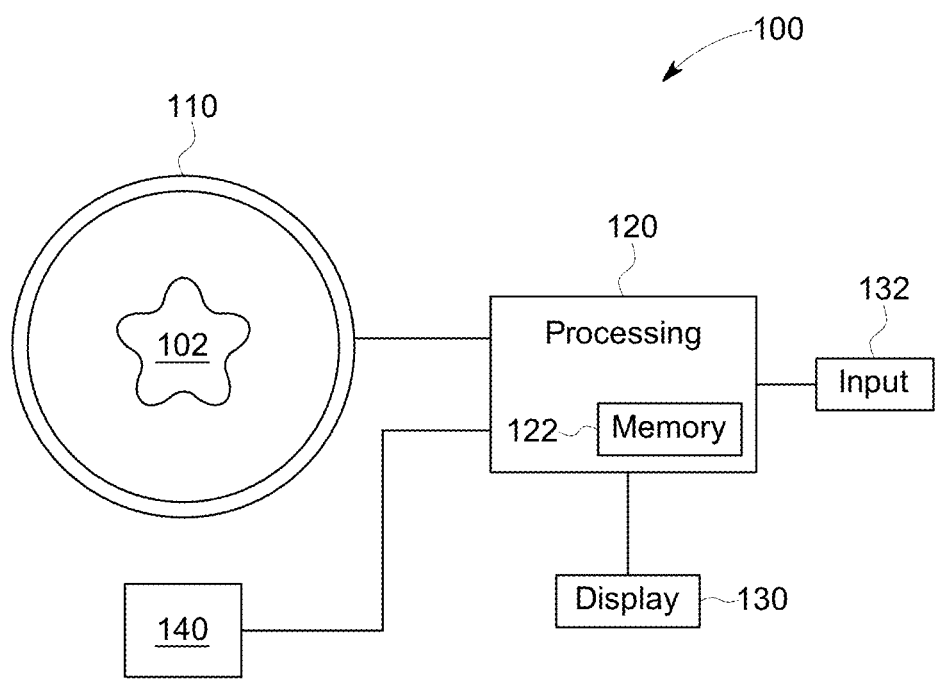
FIG. 1 provides a schematic block view of an imaging system in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" of are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide improved imaging, for example by providing improved image quality (IQ) by scanning at or near an ideal or optimal radiopharmaceutical activity level. Various embodiments, which utilize models that take into account or address variation for actual patient acquisitions, provide improved imaging relative to images taken at activity levels based on phantom studies. For example, the quality of a scan may be quantified, in a signal-to-noise ratio sense, with recommendations provided for optimal activity for better count statistics. In various embodiments, systems and/or methods are provided that are designed to learn optimal activity levels based on patient weight and/or BMI, and to recommend an optimal activity for a particular patient before injection of a radiopharmaceutical dose. Accordingly, improved IQ is provided, and dose may be reduced (e.g., if an originally planned injection would provide a significantly higher activity level than desired).

Various embodiments may be applied retrospectively to determine an optimal activity for a patient. Further, various embodiments provide an analytics too to generate smart dose regimes with respect to patient weight, metabolic rate, and/or other patient characteristics, which may be used to recommend optimal dose prospectively. Further still, various embodiments provide an organ-based dosed regime. It may be noted that, for example, via cloud computing, weekly, monthly, or other time period reports for different sites may be provided with respect to optimal activity injected in multiple patients. Accordingly, sites or facilities may analyze their scans to identify trends in activity levels at times of scanning and/or identify improvements that may be made.

Noise equivalent count (NEC) is data quality metric for PET imaging that may be understood as a characterization between administered activity and count statistics. Count statistics play an important role in detectability of low contrast features in PET imaging. Controlling the dose of injected activity close to the peak in an NEC curve improves the count statistics detected by the scanner. It may be noted that a full NEC curve for patient PET acquisition may be modelled using prompts, delayed events, detector deadtime of a single reference scan, and deadtime correlation factors. Such a method of NEC generation may be referred to as Acquisition Specific Noise Equivalent counts (ASNEC). ASNEC curves may be used to establish the optimal amount of tracer to be injected. It may be noted that actual NEC matches generally closely with an ASNEC curve generated, so that, in some embodiments, an ASNEC curve may be analyzed to identify activity levels corresponding to an NEC curve.

Various embodiments provide for improved training of practitioners in selecting dose for imaging. For example, in some embodiments, a practitioner selects acquired raw data and reconstructed PET and CT images. Next, NEC plots are generated for each frame. The plots depict activity at the start of the imaging for the frames as well as an optimal activity region. Next, suggestions for optimal activity regions or regions may be made. If the practitioner agrees with the finding, the results may be saved as part of a database, with the saved recommendations used for future patients to predict or determine an optimal dose.

Various embodiments provide systems and methods for determined, recommending, and/or implementing optimal or improved radiopharmaceutical doses based on patient profile and/or scanner type. Various embodiments provide proactive optimal dose recommendations, for example for sites or facilities that tend to administer overly high or overly dosages. Various embodiments help curb the practice of administering dosages without considering the particular scanner being used. Various embodiments provide for improved training of technologists.

A technical effect provided by various embodiments includes improved image quality. A technical effect of various embodiments includes reduction of overly large radiopharmaceutical doses. A technical effect of various embodiments includes improved training of practitioners and technologists.

FIG. 1 provides a schematic block view of an imaging system 100 in accordance with various embodiments. The depicted imaging system 100 is configured to image an object 102 (e.g., a human patient or portion thereof). The imaging system 100 of the illustrated embodiment includes at least one detector 110, a processing unit 120, a display unit 130, and a dose calibrator 140. Generally, the detector 110 is used to detect imaging information corresponding to the object 120. The processing unit 120 receives the imaging information from the detector 110, and uses the imaging information to reconstruct an image corresponding to the object 102 or a portion thereof. The display unit 130, for example, may be used to display the image that has been reconstructed by the processing unit 120. The dose calibrator 140 in various embodiments is utilized to measure an activity level of a radiopharmaceutical before the radiopharmaceutical is administered (e.g., injected into a patient).

Generally speaking, the detector 110 is configured to acquire or detect imaging information regarding the object 102 that may be provided to the processing unit 120 and used to reconstruct an image. In various embodiments, the detector 110 may detect emissions of radioactivity from the object 102, such as emissions resulting from administration of a radiopharmaceutical to a human patient. For example, the detector 110 may be a positron emission tomography PET detector. In the illustrated embodiment, the detector 110 is configured as a PET detector ring. Other modalities may be employed additionally or alternatively in various embodiments. For example, a computed tomography (CT) detector may be utilized in various embodiments. Accordingly, the system 100 may be configured for use of at least one of PET, CT, or other imaging modality.

The depicted processing unit 120 is operably coupled to the detector 110, and is configured to (e.g., programmed to) acquire the imaging information from the detector 110 that has been acquired by the detector 110. Also, the processing unit 120 is configured to reconstruct an image (e.g., an image representing the object 102 or a portion thereof such as the brain or aspects of the brain).

Image quality may be improved by performing an imaging scan at an optimal, ideal, or preferred time with respect to activity level of a radiopharmaceutical that has been administered to a patient. Accordingly, in various embodiments, the processing unit 120 is configured to (e.g., programmed to) determine, select, and/or implement an advantageous or beneficially time (e.g., with respect to a time of injection or administration of an imaging radiopharmaceutical) for performing an imaging scan. For example, the depicted processing unit 120 is configured to acquire patient scanning information, determine a target activity based on (or using) the patient scanning information, determine a target time for performing the imaging operation corresponding to (e.g., based on or using) the target activity, perform the imaging operation at the target time to acquire targeted imaging information, and reconstructing an image using the targeted imaging information.

As discussed herein, the depicted processing unit 120 acquires patient scanning information for an imaging operation to be performed. For example, the patient scanning information may be input manually (e.g., via input unit 132 which may include keyboard, touchscreen, or the like in various embodiments) by a practitioner or technician performing the scan. Additionally, or alternatively, the patient scanning information may be acquired electronically, for example from a central planning network or scheduling network that includes information regarding the scan to be performed. Generally, patient scanning information may be used to help classify or categorize a particular scanning procedure to be performed on a particular patient into a relative group for reliably or accurately identifying an ideal or preferred activity level (or range of activity levels) at which imaging information should be acquired. For example, predictive models of a desired activity level may be individually tailored for groups or categories of scans. Generally, the more specific the patient scanning information the more accurate or more highly tailored to a particular scan the predicted activity level may be; however, the more general or less restrictive the information the more past cases may be used to build a model to predict the desired activity level.

The patient scanning information may include patient specific information and/or information regarding the type of scan to be performed. For example, in various embodiments, the patient scanning information may include patient specific information regarding organ anatomy and/or metabolic rate. As another example, the patient scanning information may include information regarding the size and/or shape of the patient, such as one or more of weight, height, body mass index (BMI), or the like. Further, the patient scanning information may include information regarding the scan to be performed, such as type of scan, desired IQ, tolerable noise level, anatomical regions to be scanned, radiopharmaceutical used, scanning equipment used (e.g., type or model of detector), diagnostic purpose of the scan, or the like. Accordingly, in contrast to relying only on phantom studies, various embodiments may more specifically tailor the determination of target activity to the particular type of scan and/or individual patient characteristics of the patient to be scanned.

It may be noted that in various embodiments the patient scanning information may be used to determine which group or category of scan applies to the scan to be performed, and accordingly which model may be used. Also, the patient scanning information may be used to provide values for one or more parameters used in the models. For example, particulars regarding a scan (e.g., radiopharmaceutical used, equipment such as type of detector used, diagnostic purpose of scan, portions of a patient to be scanned, desired IQ, desired or tolerable noise level, or the like) may be included in the patient scanning information and used to select a predictive model to be employed in determining a preferred activity level for the scan. The predictive model in various embodiments is developed based on scans having similar qualities to the entered patient scanning information (e.g., similar radiopharmaceutical used, similar detector type used, similar diagnostic purpose of scan, and/or similar portions of a patient to be scanned). Further, the particular model used may utilize one or more characteristics of the scan and/or patient as an input to a formula or relationship that outputs a desired activity level. For example, the model may use the patient's weight that has been provided as part of the patient scanning information as an input, and determine the desired activity level for scanning using the patient's weight.

With the patient scanning information acquired, the depicted processing unit 120 next determines a target activity based on the patient scanning information. Generally, the target activity specifies or corresponds to an activity level of a radiopharmaceutical at which the imaging scan is to be performed. The activity level may be an ideal activity level, an optimal activity level, or an improved activity level. The activity level may be specified as an individual target value, or as a range of values. For example, the processing unit 120 may utilize one or more of a model, formula, or other mathematical relationship, or a database, to determine the target activity. The model can be built based on previous cases. The model or mathematical relationship may be built based on previously acquired imaging results. For example, peak activity levels (or activity level corresponding to peak NEC or other metric) may be determined for past cases, and used to build the model. The model may then be used to predict or determine activity levels that correspond to peak NEC (or other peak metric or target metric) for the scan to be performed. Different models may be developed for different types of scans (e.g., scans for different diagnostic purposes or for different portions of the body) and/or for different types of equipment.

Figure 2:
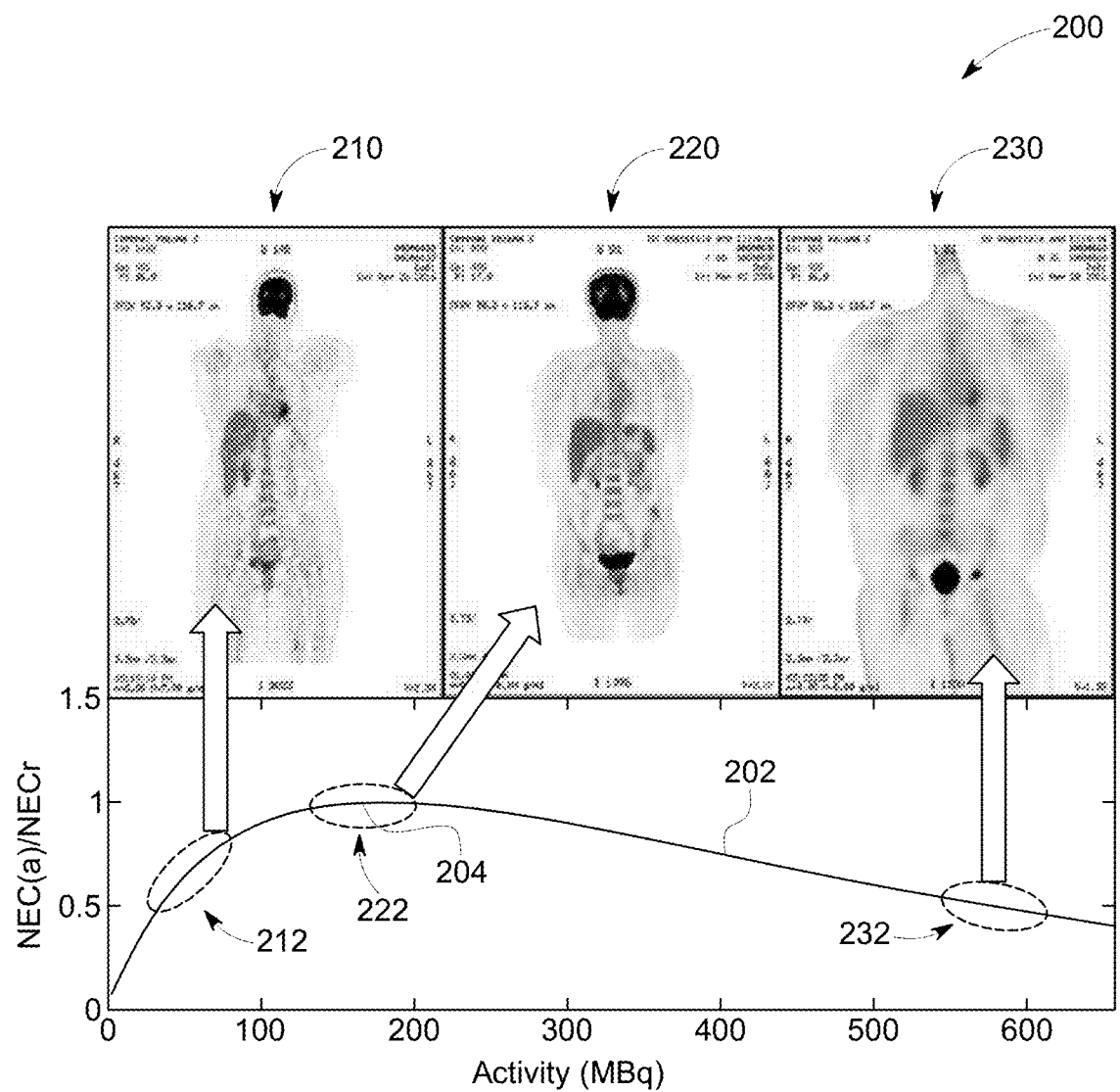
FIG. 2 provides a plot of NEC values and activity levels in accordance with various embodiments.

In various embodiments, the processing unit 120 determines the target activity based on a peak noise equivalent count (NEC). For example, the processing unit 120 may identify the target activity that corresponds to a peak NEC predicted using a model or other relationship applicable to a particular scan to be performed. FIG. 2 provides a plot 200 of NEC values for various activity levels for an example scanning procedure, along with corresponding example images for particular activity levels. NEC plays an important role in determining signal to noise ratio (SNR), and accordingly plays an important role in IQ. Generally, the optimal activity level is the activity level having the peak NEC, in order to provide good count statistics.

In the example, depicted in FIG. 2, an NEC curve 202 is plotted with NEC level as the y-axis and activity level as the x-axis. The NEC level may be expressed, for example, as a relative value, a normalized value, or as a ratio. As seen in FIG. 2, the NEC curve 202 has a peak 204 that occurs in a middle portion of the plotted activity levels. It may be noted that activity level is inversely proportional to time, with activity level decreasing as a radiopharmaceutical decays. In the illustrated example, three images are depicted, namely a first image 210 corresponding to a first activity level range 212, a second image 220 corresponding to a second activity level range 222, and a third image 230 corresponding to a third activity level range 232. Each activity level corresponds to a range of time after administration of a radiopharmaceutical to a patient at which the patient was imaged.

The first image 210 was reconstructed using imaging information acquired over the first activity level range 212. The first activity level range 212 includes lower activities than the second activity level range 222 and the third activity level range 232, and accordingly corresponds to imaging information scanned with a longer elapsed time after administration of the radiopharmaceutical than the elapsed time for the imaging information acquired the second activity level range 222 and the third activity level range 232 for the second image 220 and third image 230, respectively.

The second image 220 was reconstructed using imaging information acquired over the second activity level range 222. The second activity level range 222 includes higher activities than the first activity level range 212 but lower activities than the third activity level range 232, and accordingly corresponds to imaging information scanned with a shorter elapsed time after administration of the radiopharmaceutical than the elapsed time for the imaging information acquired the first activity level range 212 (used for the first image 210), but a shorter elapsed time than for the third activity level range 232 (used for the third image 230). It may be noted that the peak activity level 204 is included in the second activity level range 222.

The third image 230 was reconstructed using imaging information acquired over the third activity level range 232. The third activity level range 232 includes higher activities than the second activity level range 222 and the first activity level range 212, and accordingly corresponds to imaging information scanned with a shorter elapsed time after administration of the radiopharmaceutical than the elapsed time for the imaging information acquired the second activity level range 222 and the first activity level range 212 for the second image 220 and first image 210, respectively.

As seen in FIG. 2, the IQ for the second image 220, which was reconstructed using information acquired during the second activity level range 222, which included the activity level corresponding to the peak 204 of the NEC curve 202 is better than the IQ for the first image 210 or the third image 220, which were acquired at activity levels that do not correspond to the peak NEC value. Accordingly, for the example depicted in FIG. 2, the IQ is best when acquiring imaging information at or near the highest NEC value. The processing unit 120 in various embodiments is configured to determine the target activity based on a peak NEC (e.g., a predicted peak or maximum NEC value). An ideal activity level (or ideal activity) or target activity level (or target activity) may be understood as that activity level at which the NEC value (or other metric) is maximized or at a peak. Such an ideal or target activity may also be referred to as a peak activity. Similarly, an ideal, target, or peak time for acquiring imaging information may be understood as a time range that includes the peak activity, or a time during with the NEC value (or other metric) is at a peak or maximum. For example, the target time may be centered around the peak.

As discussed herein, in various embodiments, the processing unit 120 determines the target activity based on a mathematical model developed from historical or previously obtained images. The target activity (e.g., activity level corresponding to peak NEC value) in various embodiments is determined using at least one parameter value defined or supplied by the patient scanning information, with the at least one parameter value used in connection with a mathematical model developed from previously acquired images. For example, the patient scanning information in various embodiments includes a patient weight that specifies the weight of the patient being scanned. The model employed to determine target activity may use weight as an input.

Figure 3:
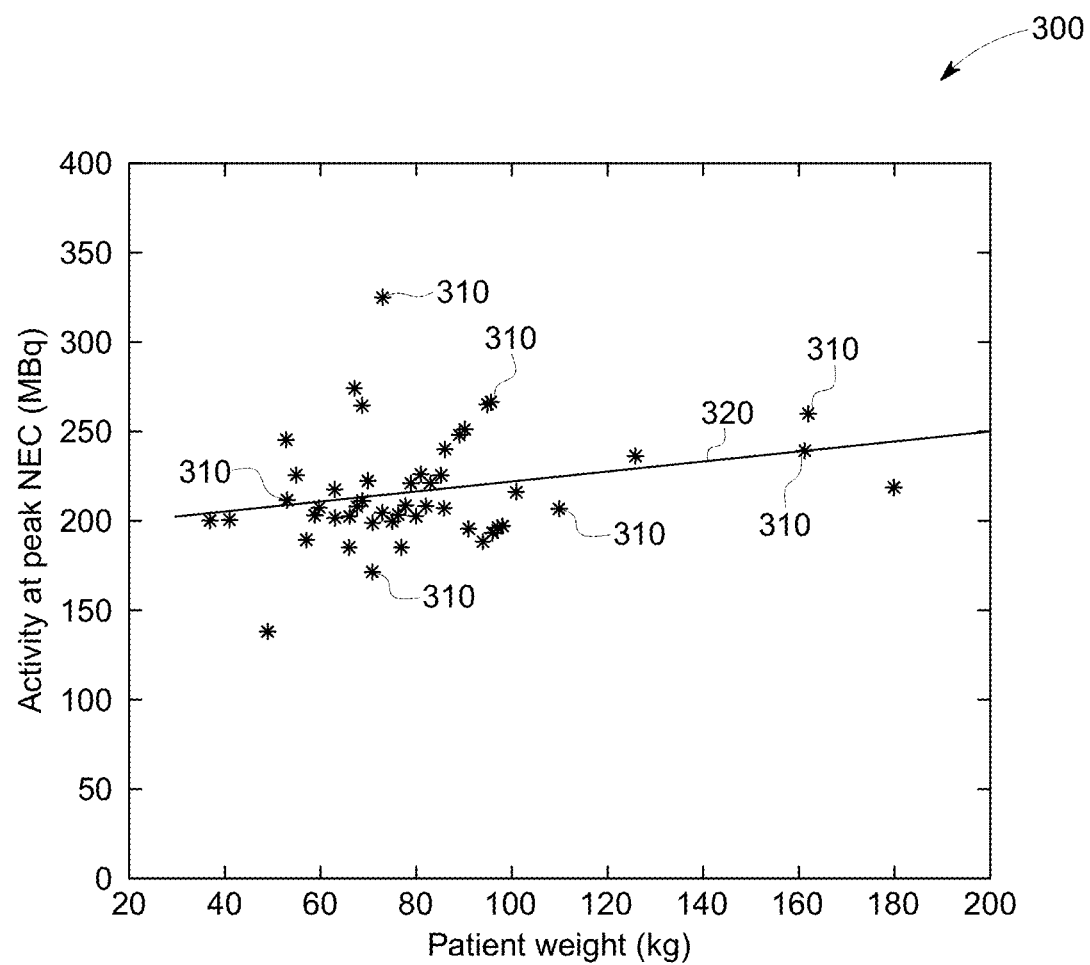
FIG. 3 provides a plot of activity level in accordance with various embodiments.

In various embodiments, the target activity is expressed as a function (e.g., linear function) of weight. FIG. 3 provides a plot 300 of activity level as a function of patient weight. As seen in FIG. 3, the x-axis corresponds to patient weight and the y-axis corresponds to the activity at peak NEC. Data points 310 are compiled from previous imaging results (e.g., activity levels corresponding to peak NEC values for previous imaging procedures), and used to produce a curve 320. It may be noted that the data points may be compiled using frames that exclude one or more of the brain, the bladder, or extremities. In the illustrated embodiment, the curve 320 is a linear fit curve generated using the data points 310. For example, the optimal activity at the start of a scan may be expressed as $A_{Opt}=a+b*w$, where $A_{Opt}$ is the optimal activity at the start of the scan, a and b are constants, and w is the weight of the patient being scanned. The particular values of a and b are specified by the model, and may be based on historically acquired scanning information using similar equipment and/or for similar types of scans as the scan to be performed. Similarly, based on the half-life or decay rate of the administered pharmaceutical, as well as the time between injection and scanning (e.g., a predetermined time such as 60 minutes from injection of radiopharmaceutical until acquisition of scanning information) an injected activity level may be determined based on patient weight.

With continued reference to FIG. 1, with the target activity determined, the processing unit 120 in various embodiments next determines a target time for performing the imaging operation corresponding to the target time. For example, the target time may be determined based on the target activity. For example, the target activity may be expressed as a single activity level (e.g., an activity level corresponding to peak NEC). Then, a corresponding target time value is determined. The time range for acquiring the imaging information may then be determined based on the target time value. For example, the time range may be centered about the target time value. As another example, the target time value may be used as a starting time for beginning acquisition of imaging information. As one more example, an offset may be employed, so that the acquisition begins a predetermined amount of time before the target time value. Alternatively, in other embodiments, the target activity may be expressed as a range of activity levels, with a corresponding target time range determined using the endpoints of the range of activity levels of the target activity.

The target time in various embodiments may be used based on the target activity level, and a half-life or other decay characteristic of a radiopharmaceutical. For example, by knowing the current or measured activity of a radiopharmaceutical, along with the decay rate of the radiopharmaceutical, the amount of time required to elapse from a current time to the time at which the radiopharmaceutical will be at the desired or target activity level may be determined. Then, by knowing the expected overall time of the scan, a time range for performing the scan may be determined relative to the current time. For example, for a scan to be performed with the peak NEC value at the mid-point of the time range of scanning, the time at which the acquisition imaging is initially started may be expressed as $T_{start}=T_{peak}-0.5*T_{scan}$, where $T_{start}$ is an elapsed time to the beginning of the acquisition of imaging information, $T_{peak}$ is a determined elapsed time to the target activity level (determined using a current activity level and decay characteristic of the radiopharmaceutical), and $T_{scan}$ is the amount of time over which imaging information will be acquired. Other starting times may be employed in various embodiments, such as starting the scan at $T_{peak}$, or starting the scan a predetermined amount of time before $T_{peak}$.

Accordingly, with the activity level at the time of administration known, the decay properties of the radiopharmaceutical known, and the desired or target activity previously determined, the time at which to acquire imaging information may be determined. It may be noted that in various embodiments, the activity level at the time of administration is determined using a dose calibrator. The example system 100 depicted in FIG. 1 includes a dose calibrator 140. The dose calibrator 140 is configured to determine a pre-injection activity level for the radiopharmaceutical to be administered for use in imaging.

It may be noted that, in a simple model of how FDG imaging works, after a period of time all of the FDG has been extracted from blood by tissue, and may be understood as metabolically "stuck" there until it decays. However, in practice, there is leaking of FDG, which varies between tissues and/or between tissue and cancer cells, such that the activity distribution after one period of time (e.g., 115 minutes) is not the same as at a previous time (e.g., 60 minutes). Accordingly, as another example, the target time corresponding to the target activity level may be predetermined. Then, instead of determining a time for scanning based on a known activity level, an activity level to be used at the time of injection may be determined based on a known time from injection to scanning to provide the target activity level during scanning. For instance, a site for administering scans may use a predetermined time from injection to scanning, for example based on experience at that particular site. Thus, in some embodiments, with the target time from injection to initiating a scan known or predetermined, the activity level provided at injection may be selected to provide the target activity during the scan.

The dose calibrator 140 may include a display that provides the activity level, or may communicate the activity level to the processing unit 120. The processing unit 120 than determines the target time using the pre-injection activity level and a decay characteristic (e.g., half-life) for the radiopharmaceutical. For example, the processing unit 120 may determine the activity level at the time of administration or injection (or other reference point in time) and determine a time to initiate imaging information acquisition relative to the time of injection (or other reference point in time).

After the target time is determined, the processing unit 120 performs the imaging operation at the target time to acquire targeted imaging information. In various embodiments, the processing unit 120 may be understood to perform the imaging operation at the target time by, for example, providing an instruction to a human operator to operate an imaging system to acquire imaging information at the target time (e.g., by providing a display including the target time expressed as one or more of an absolute, a time relative to a particular reference such as relative to a time of injection, or a countdown with the scan to commence when the countdown reaches zero). As another example, the processing unit 120 may perform the imaging operation at the target time by providing control instructions to an imaging system that cause the imaging system to acquire imaging information at a desired time. As discussed herein, as the targeted imaging information has been acquired at a time (e.g., over a time range) including or corresponding to a peak NEC value or other predetermined metric (e.g., as predicted or determined using a model based on prior similar imaging operations), the targeted imaging information provides improved IQ relative to imaging information that may have been acquired at different times.

With the targeted imaging information acquired, the processing unit 120 may next reconstruct an image using the targeted imaging information. The reconstructed image may then be displayed to a practitioner for diagnostic purposes. For example, in the illustrated embodiment, the display unit 130 is communicably coupled to the processing unit 120 and receives the image (or corresponding data) from the processing unit 120, with the display unit 130 configured to display the reconstructed image. The display unit 130 may be used for other purposes additionally or alternatively. For example, the display unit 130 may be used in connection with an input unit (e.g., keyboard, touchscreen) for interactive entry of patient scanning information by a practitioner. As another example, the display unit 130 may display instructions, such as a time to start acquiring imaging information, to a practitioner.

In various embodiments the processing unit 120 includes processing circuitry configured to perform one or more tasks, functions, or steps discussed herein. It may be noted that "processing unit" as used herein is not intended to necessarily be limited to a single processor or computer. For example, the processing unit 120 may include multiple processors, ASIC's, FPGA's, and/or computers, which may be integrated in a common housing or unit, or which may distributed among various units or housings. It may be noted that operations performed by the processing unit 120 (e.g., operations corresponding to process flows or methods discussed herein, or aspects thereof) may be sufficiently complex that the operations may not be performed by a human being within a reasonable time period. For example, the acquisition of signals or imaging information, the determination of a target activity, the determination of a target time, the control of imaging acquisition equipment, and the reconstruction of an image may rely on or utilize computations that may not be completed by a person within a reasonable time period. In the illustrated embodiment, the processing unit 120 includes a tangible, non-transitory memory 122 for storage of, among other things, instructions for causing the processing unit 120 to perform one or more steps or tasks discussed herein.

It may be noted that in various embodiments, different portions of the object 102 (e.g., human patient) may be scanned at different times, or in stages. For example, a first portion of the body may be scanned over a first time range to provide a first frame of imaging information, a second portion of the body may be scanned over a second time range commencing immediately or nearly immediately after the first time range to provide a second frame of imaging information, and so on. The various frames may be reconstructed and added together to provide a composite image. The object 102 and at least one detector 110 may be moved relative to each other to transition from one stage to the next. In various embodiments, the imaging operation is performed in a series of frames, with the processing unit 120 configured to determine a frame target activity for at least some of the frames on a frame-by-frame basis. For example, in some embodiments, the processing unit 120 may determine a distinct frame target activity for each frame, with the frame target activities used to determine scanning times. In some embodiments, the processing unit 120 is further configured to determine an order for the frames to be imaged in based on the corresponding frame target activities. For instance, a frame with a higher (or highest) target activity level corresponding to peak NEC level may be acquired before a frame with a lower (or lowest) target activity level corresponding to peak NEC level. Accordingly, those frames with higher target activity levels may be imaged generally before those frames with lower target activity levels, so that IQ is optimized. In some embodiments, the frames may be hierarchically ranked according to target activity level and imaged in order; however, in other embodiments, other considerations, such as the proximity of frames to each other may be used in selecting order of frames in conjunction with activity levels. It may further be noted that in some embodiments, some frames may be analyzed for activity level on a frame-by-frame basis while others are not.

Figure 4:
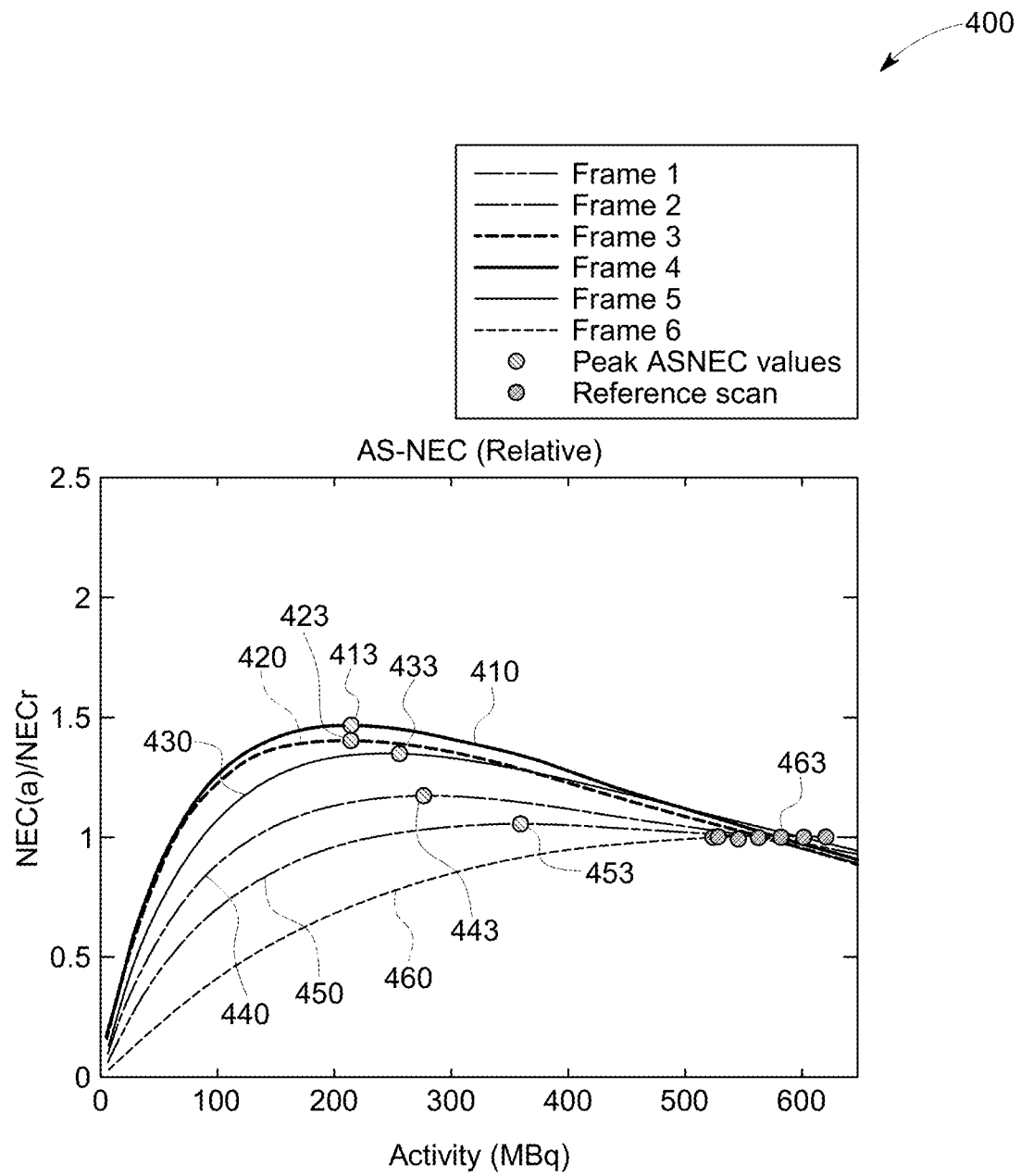
FIG. 4 provides a plot of activity levels for a series of frames in accordance with various embodiments.

FIG. 4 provides a plot 400 of activity levels for a series of frames. The plot 400 includes a series of curves of NEC plotted against activity level. As seen in FIG. 4, the plot 400 includes a first curve 410 for a first frame, a second curve 420 for a second frame, a third curve 430 for a third frame, a fourth curve 440 for a fourth frame, a fifth curve 450 for a fifth frame, and a sixth curve 460 for a sixth frame. Each curve also includes a peak value (a first peak 413 for the first curve 410, a second peak 423 for the second curve 420, a third peak 433 for the third curve 430, a fourth peak 443 for the fourth curve 440, a fifth peak 453 for the fifth curve 450, and a sixth peak 463 for the sixth curve 460). Accordingly, the curve peaks may be used to select corresponding times for scanning the patient. In some embodiments, an average or other combination of times corresponding to the curve peaks may be used. In other embodiments, the curve peaks may be used to select an order in which the frames are acquired (e.g., with frames having peaks at higher activity levels imaged before frames with lower activity levels). The order may also be affected by relative diagnostic importance. For example, if a frame for a particular scan is of higher diagnostic relevance than one or more other frames, that frame may be imaged at a time corresponding to the peak of its NEC curve preferentially over other frames. It may be noted that in some embodiments, separate models may be used for each frame, with the models developed separately frame-by-frame. It may be noted that, when developing models, certain frames may be used while others are disregarded. For example, frames corresponding to the brain, bladder, and/or extremities may be disregarded or given less weight in developing models in some embodiments.

Figure 5:
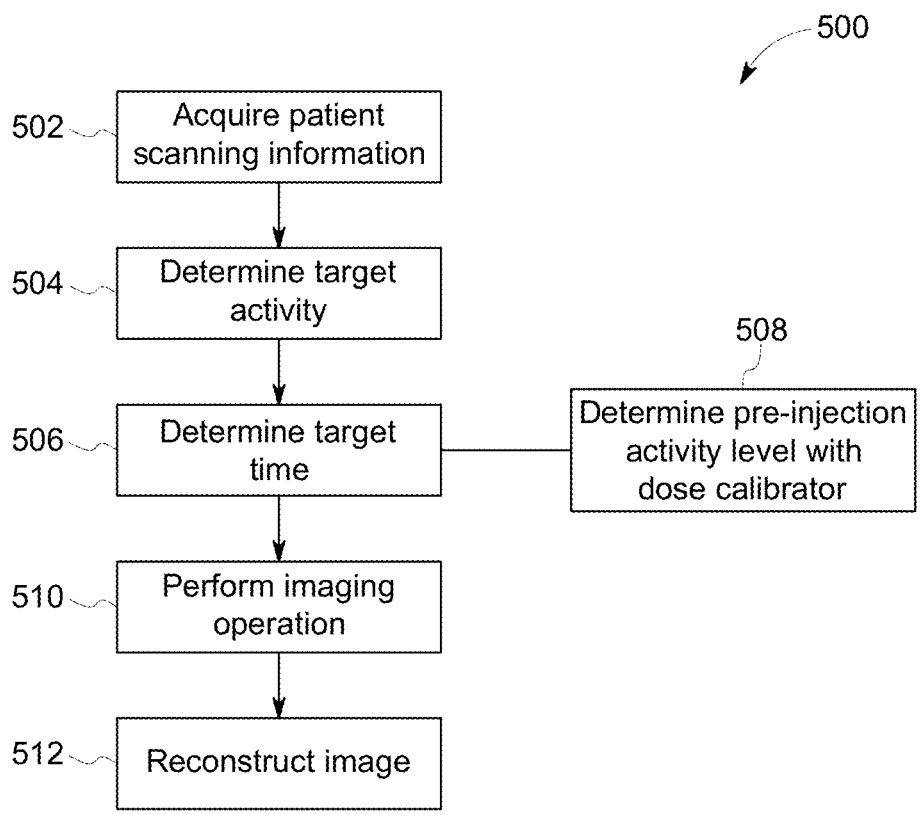
FIG. 5 illustrates a flowchart in accordance with various embodiments.

FIG. 5 illustrates a flowchart of a method 500. The operations of FIG. 5 may be implemented by one or more processors (e.g., processing unit 120) executing program instructions stored in memory (e.g., memory 122). The method 500, for example, may employ structures or aspects of various embodiments (e.g., systems and/or methods) discussed herein, such as the system 100. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 500 may be used as one or more algorithms to direct hardware (e.g., processing unit 120) to perform one or more operations described herein. It should be noted, other methods may be used, in accordance with embodiments herein.

At 502, patient scanning information is acquired (e.g., by at least one processor such as processing unit 120). The patient scanning information is for a particular scan to be performed. Generally, as discussed herein, the patient scanning information describes the patient to be scanned and/or the scanning procedure to be performed. The patient scanning information in various embodiments is used to select (and/or build or modify) a model to be used to determine a target activity level, and/or to provide one or more inputs of values used by a model for determining target activity level. For example, the patient scanning information may include patient weight, with the desired activity level expressed as a function of patient weight. Other parameters may be used additionally or alternatively in various embodiments. In various embodiments, patient scanning information may include one or more of patient height, BMI, diagnostic purpose of scan, anatomical information regarding organs to be scanned, type of detector used to perform scan, duration of scan, radiopharmaceutical used in conjunction with scan, desired IQ, or tolerable noise level, among others. The patient scanning information may be provided via manual input and/or communicated electronically.

At 504, a target activity is determined (e.g., by at least one processor such as processing unit 120). The target activity describes or corresponds to an activity level that is ideal, optimal, or preferred for scanning, for example by providing an ideal, optimal, or improved IQ. In various embodiments, the target activity is determined based on a peak NEC (e.g., the target activity is that activity for which the NEC reaches a maximum as predicted by a model). The target activity is determined based on (or using) the patient scanning information. For example, the target activity may be determined in various embodiments using a mathematical model or relationship that utilizes at least aspects of the patient scanning information. For example, the model may correspond to a particular type (or types) of diagnostic purpose of scan and/or scanning equipment, and the patient scanning information may be used to determine which model to use for a particular scan to be performed. As another example, the patient scanning information may provide a value for a parameter (e.g., patient weight) used as an input when using the model. In various embodiments, the model may be predetermined based on historical or previously acquired images. It may be noted that the model may be updated, or trained, with additional data points as more scans are performed, for example to help tailor the model to a particular facility or equipment type.

At 506, a target time is determined for performing the imaging operation corresponding to (e.g., based on or using) the target activity. In various embodiments, a reference time (e.g., time of injection) is selected at which the activity of the radiopharmaceutical is known. Then, the amount of time for the radiopharmaceutical to decay to the target activity is determined. The target time for performing the scan may then be determined using the amount of time for the activity to decay to the target level. For example, the amount of time for the activity to decay to the target level may be used as a time to initiate acquisition of scanning information. As another example, the scan may be initiated a predetermined amount of time before the time at which the radiopharmaceutical will decay to the target activity level. As one more example, the amount of time to decay to the target level may be used as a midpoint of a time range used to acquire imaging information. In other embodiments, the target time (or time from injection to scanning) may be initially determined independently of target activity (e.g., based on pratictioner preferences for a given site and/or procedure), and the injection activity level selected to provide the target activity level during scanning based on the previously determined time from injection to scanning. In various embodiments, the activity level at the predetermined time (e.g., time of injection) may be determined via a dose calibrator. For example, at 508 of the depicted example, a dose calibrator is used to determine a pre-injection activity level, with the target time determined using the pre-injection activity level and a known decay characteristic (e.g., half-life) of the radiopharmaceutical.

At 510, the imaging operation is performed to acquire target imaging information at the target time. In various embodiments, the target time may be displayed to a practitioner or operator, prompting the operation of scanning equipment to acquire the imaging information. In some embodiments, the target time may be automatically or autonomously implemented. The imaging operation may include acquiring PET and/or CT imaging information in various embodiments. It may be noted that in various embodiments that imaging operation may be performed to acquire frames of imaging information, with each frame corresponding to a different portion of the body (e.g., each frame corresponding to a portion of the body fitting within a window along the axial length of the body corresponding to the field of view of the detector). Further, individual frame target activities may be determined for at least some of the frames. Further still, in some embodiments, an order for the frames may be determined, with the order specifying the sequential order of acquisition for frames for which imaging information is acquired. The order may be determined based on (or using) the corresponding frame target activities.

At 512, an image is reconstructed using the targeted imaging information. As the targeted imaging information was acquired at an ideal, optimal, or improved activity level (e.g., corresponding to a determined or predicted NEC peak), the target imaging information provides improved IQ for the image reconstructed at 512.

Figure 6:
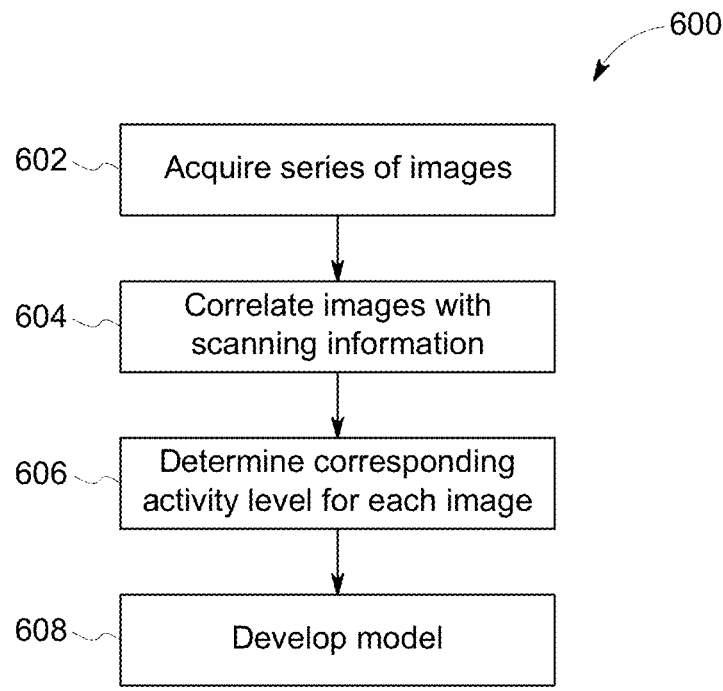
FIG. 6 illustrates a flowchart in accordance with various embodiments.

As discussed herein, a model used to determine a target activity level or range may be developed or built using imaging information from previous scans. FIG. 6 illustrates a flowchart of a method 600. The operations of FIG. 6 may be implemented by one or more processors (e.g., processing unit 120) executing program instructions stored in memory (e.g., memory 122). The method 600, for example, may employ structures or aspects of various embodiments (e.g., systems and/or methods) discussed herein, such as the system 100. A model developed in connection with the method 600 may be utilized by systems and/or methods discussed herein, such as the system 100 or the method 500. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 600 may be used as one or more algorithms to direct hardware (e.g., processing unit 120) to perform one or more operations described herein. It should be noted, other methods may be used, in accordance with embodiments herein.

At 602, a series of images are acquired across a population of patients. The images may be archived or stored in a collection over time. In some embodiments, the images are acquired from a number of facilities and sources and from a number of different practitioners for use in developing a general model or models that may be used at different facilities. In some embodiments, the images are collected from a single facility or single practice group for use in developing a model or models tailored for that facility or practice group.

At 604, each image from the series is correlated with scanning information corresponding to the image. The scanning information may be collected contemporaneously with each scan, with the scanning information for a given scan cross-referenced or otherwise associated with the imaging information and/or a reconstructed image for the given scan. As discussed herein, patient scanning information may be used to help classify or categorize a particular scanning procedure into a relative group for reliably or accurately identifying an ideal or preferred activity level (or range of activity levels) at which imaging information should be acquired. As also discussed herein, the patient scanning information for each scan may include patient specific information regarding the patient for that particular scan (e.g., information regarding organ anatomy, weight, height, BMI, or the like) and/or include information regarding the particular scan that has been performed (e.g., type of scan, desired IQ, tolerable noise level, anatomical regions to be scanned, radiopharmaceutical used, scanning equipment used, diagnostic purpose of the scan, or the like).

At 606, a corresponding activity level for a predetermined metric (e.g., peak NEC) is determined for each image. For example, a full NEC curve for a given patient PET acquisition may be modelled using prompts, delayed events, detector deadtime of a single reference scan, and deadtime correlation factors, and the activity corresponding to the peak NEC identified using the curve. In various embodiments, the activity level corresponding to the peak NEC for each image may be stored and cross-referenced to the particular image and corresponding scanning information.

At 608, a model is developed based on the corresponding predetermined metric (e.g., peak NEC) for each of the images. For example, a mathematical relationship between weight (and/or other parameter value determined from the acquired scanning information) and activity level for peak NEC (or other metric) may be determined. In some examples, data points providing a plot of activity level for peak NEC plotted for patient weights are used in connection with a curve fitting process to provide the model or mathematical relationship. For example, a linear relationship between patient weight and activity level for peak NEC may be determined using such data points. It may be noted that the particular data points to be used for a given model may be selected based on similar procedures and/or equipment, with different models developed for different scanning procedures and/or different equipment. Further, the model may be developed for a particular facility or practice group, or may be generalized across facilities and/or practice group. It may further be noted that the model may be updated or modified based on subsequently acquired images. Accordingly, the model may be understood as learning or being trained using subsequently acquired images. Further still, the model may be developed and/or applied on a frame-by-frame basis as discussed herein.

As discussed herein, systems and methods disclosed herein provide, for example, tools that can (1) retrospectively report to a site the efficacy of tant site's administered dose strategy (e.g., would imaging improve from a SNR standpoint with olower or higher injected doses) and/or (2) develop a predictive tool to prospectively recommend administered doses based on patient characterstics (e.g., height, weight, BMI, body part under evaluation, or the like) for future patients. It may be noted that artificial intelligence or deep learning technologies may be employed in developing the predictive tool.

For example, based on viewing results (e.g., results similar to those depicted in FIG. 4), a practitioner may notice that optimal imaging occurs at substantially lower doses than the doses actually used. If such higher than optimal doses were observed regularly or as a trend, the practitioner may then improve imaging quality by lowering dose.

As another example, activity at peak NECR observations from a number of scans may be plotted against one or more independent variables. (For instance, in FIG. 3 a single independent variable of patient weight was employed.) Fitting the data (e.g, by regression) as a function of the independent variable or independent variables allows prediction of activity at peak NECT for a particular patient before the patient is imaged. Knowing the desired activity and desired inject-to-scan delay time, the injected activity required to provide the target activity during scanning may be calculated.

Figure 7:
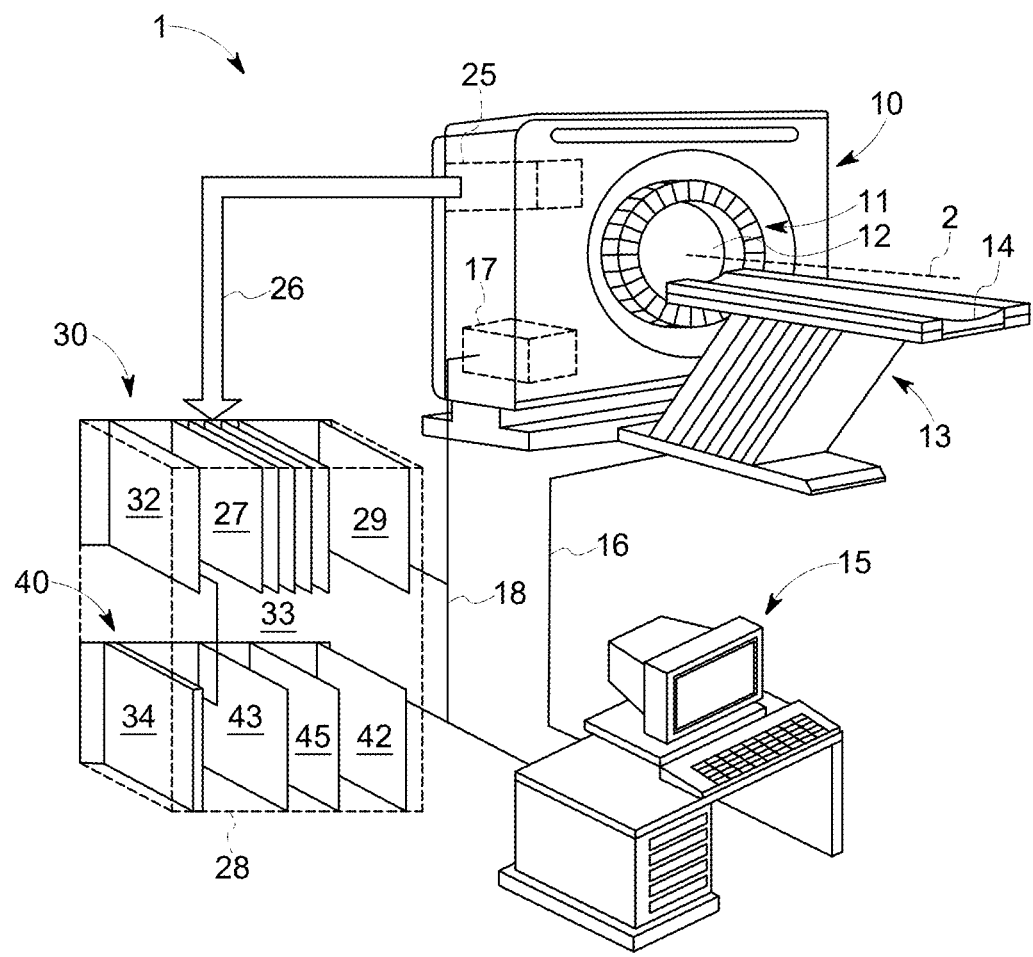
FIG. 7 illustrates an imaging system in accordance with various embodiments.
Figure 8:
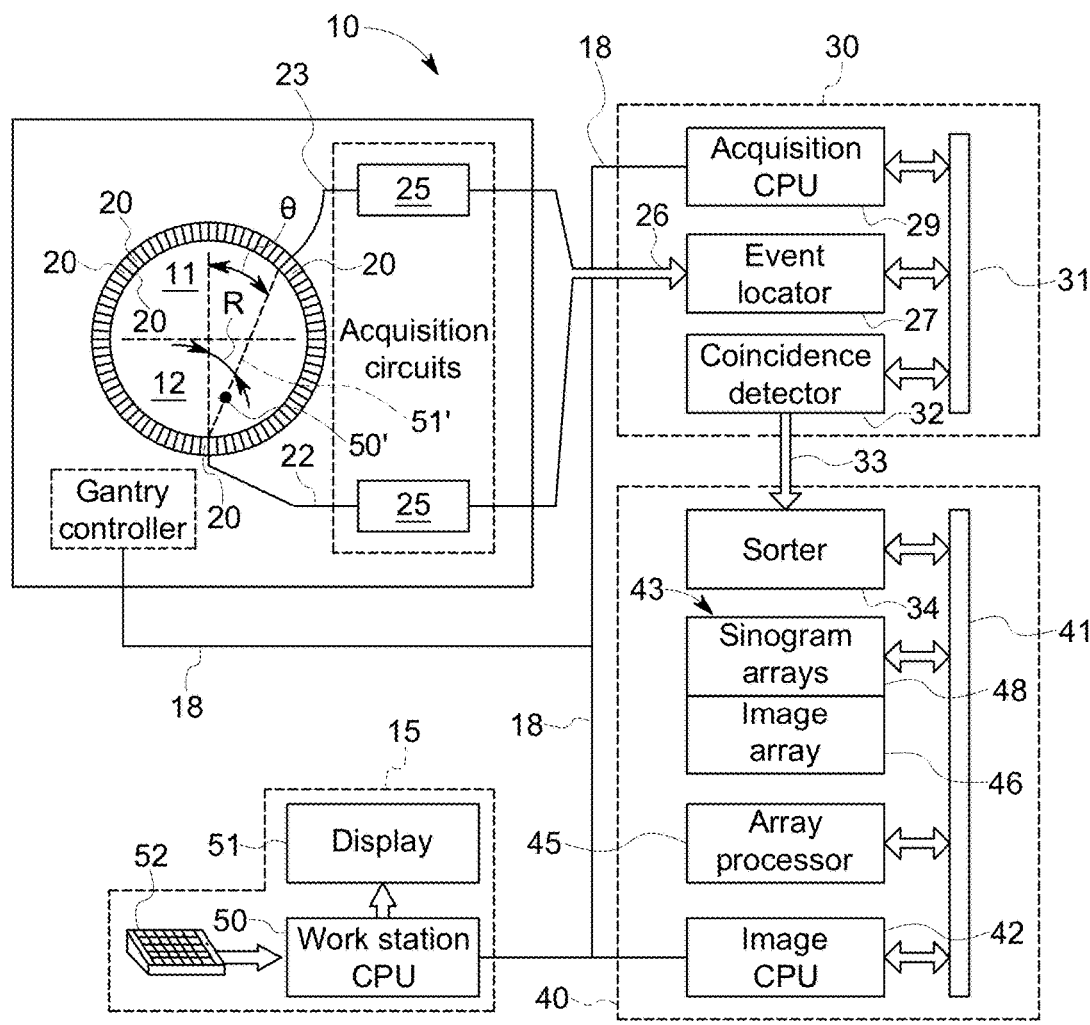
FIG. 8 is a schematic diagram of the imaging system of FIG. 7.
Figure 9:
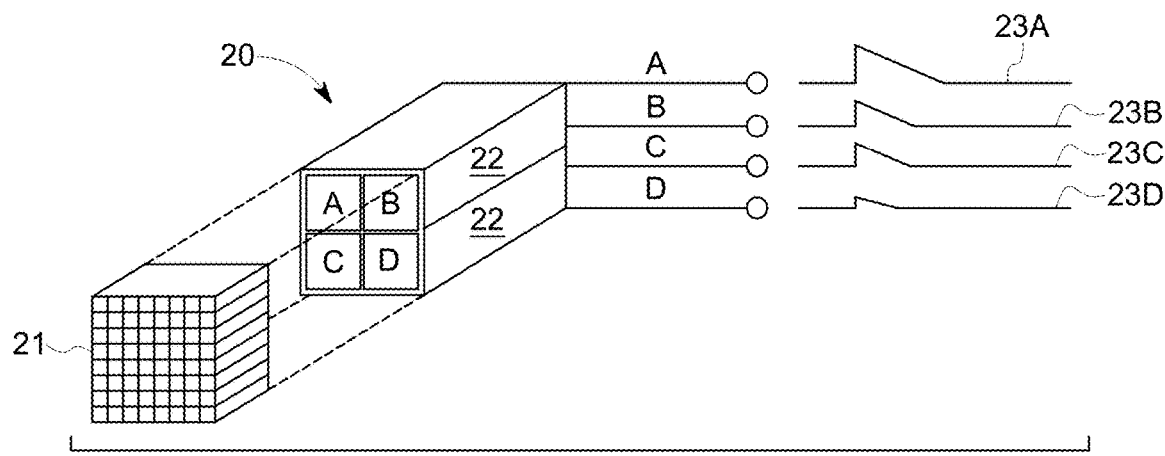
FIG. 9 illustrates an example of a detector module which forms part of the imaging system in accordance with various embodiments.

FIGS. 7-9 illustrate a PET imaging system with which various embodiments described herein may be employed. In other embodiments, crystal arrays as discussed herein may be utilized with other imaging systems (e.g., imaging systems configured for one or more additional or alternative modalities). FIG. 7 illustrates a PET scanning system 1 including a gantry 10 that supports a detector ring assembly 11 about a central opening or bore 12. The detector ring assembly 11 in the illustrated embodiments is generally circular and is made up of plural rings of detectors spaced along a central axis 2 to form a cylindrical detector ring assembly. In various embodiments, the detector ring assembly 11 may include 5 rings of detectors spaced along the central axis 2. A patient table 13 is positioned in front of the gantry 10 and is aligned with the central axis 2 of the detector ring assembly 11. A patient table controller (not shown) moves the table bed 14 into the bore 12 in response to commands received from an operator work station 15 through a communications link 16. A gantry controller 17 is mounted within the gantry 10 and is responsive to commands received from the operator work station 15 through a second communication link 18 to operate the gantry.

As shown in FIG. 8, the operator work station 15 includes a central processing unit (CPU) 50, a display 51, and a keyboard 52. An operator may use the keyboard to control the calibration of the PET scanner, the configuration of the PET scanner, and the positioning of the patient table for a scan. Also, the operator may control the display of the resulting image on the display 51 and/or perform image enhancement functions using programs executed by the work station CPU 50.

The detector ring assembly 11 includes a number of detector modules. For example, the detector ring assembly 11 may include 36 detector modules, with each detector module including eight detector blocks. An example of one detector block 20 is shown in FIG. 9. The detector blocks 20 in a detector module may be arranged, for example, in a 2×4 configuration such that the circumference of the detector ring assembly 11 is 72 blocks around, and the width of the detector assembly 11 is 4 detector blocks wide. Each detector block 20 may include a number of individual detector crystals. In the illustrated embodiment, the array of detector crystals 21 is situated in front of four photosensors 22. The photosensors 22 are depicted schematically as photomultiplier tubes; however, it may be noted that SiPM's may be employed in various embodiments. Other configurations, sized and numbers of detector crystals, photosensors and detector modules may be employed in various embodiments.

During a PET scan, an annihilation photon may impact one of the detector crystals 21. The detector crystal 21, which may be formed, for example of lutetium yttrium silicate (LYSO) or bismuth germinate (BGO), for example, converts the annihilation photon into a number of photons which are received and detected by the photosensors. The photons generated by a detector crystal generally spread out to a certain extent and travel into adjacent detector crystals such that each of the four photosensors 22 receives a certain number photons as a result of an annihilation photon impacting a single detector crystal 21.

In response to a scintillation event, each photosensor 22 produces a signal 23A-23D on one of the lines A-D, as shown in FIG. 9, which rises sharply when a scintillation event occurs and then tails off exponentially. The relative magnitudes of the signals are determined by the position in the detector crystal array at which the scintillation event took place. The energy of the annihilation photon which caused the scintillation event determines the total magnitude of the four signals. The time that the signal begins to rise is determined by when the scintillation event occurs and the time required for photons to travel from the position of the scintillation event to the photosensors. The example depicted in FIG. 9 provides an example based on a vacuum photodetector; however, it may be noted that certain principles disclosed herein may also be applied to SiPM detectors generally.

As shown in FIG. 8, a set of acquisition circuits 25 is mounted within the gantry 10 to receive the four signals from the detector block 20. The acquisition circuits 25 determine timing, energy and the event coordinates within the array of detector crystals using the relative signal strengths. The results are digitized and sent through a cable 26 to an event locator circuit 27 housed in a separate cabinet 28. Each acquisition circuit 25 also produces an event detection pulse which indicates the exact moment the scintillation event took place.

The event locator circuits 27 form part of a data acquisition processor 30 which periodically samples the signals produced by the acquisition circuits 25. The data acquisition processor 30 has an acquisition CPU 29 which controls communications on the local area network 18 and a bus 31. The event locator circuits 27 assemble the information regarding each valid event into a set of digital numbers that indicated when the event took place and the identity of the detector crystal 21 which detected the event. The event locator circuits 27, for example, may use a detector position map to map a pair of coordinates to the detector 21 which detected the event.

The event data packets are transmitted to a coincidence detector 32 which is also part of the data acquisition processor 30. The coincidence detector 32 accepts the event data packets from the event locator circuits 27 and determines if any two of them are in coincidence. Coincidence is determined by a number of factors. For example, time markers in each event data packet may be required to be within a specified time period of each other, e.g., 6 nanoseconds. As another example, the locations indicated by the two event data packets may be required to lie on a straight line which passes through the field of view (FOV) in the scanner bore 12. Events which cannot be paired are discarded, but coincident event pairs are located and recorded as a coincidence data packet that is transmitted through a serial link 33 to a sorter 34. The format of the coincidence data packet may be, for example, a thirty-two bit data stream which includes, among other things, a pair of digital numbers that precisely identify the locations of the two detector crystals 21 that detected the event.

The sorter 34, which may include a CPU and which forms part of an image reconstruction processor 40, receives the coincidence data packets from the coincidence detector 32. The function of the sorter 34 is to receive the coincidence data packets and allocate sinogram memory for the storage of the coincidence data. The set of all projection rays that point in the same direction ($\theta$) and pass through the scanner's field of view is a complete projection, or "view", which makes a set of sinogram. The distance (R) between a particular projection ray and the center of the field of view locates that projection ray within the view. As shown in FIG. 8, for example, an event 50' occurs along a projection ray 51' which is located in a view at the projection angle $\theta$ and the distance R. The sorter 34 counts all of the events that occur on this projection ray (R, θ) during the scan by sorting out the coincidence data packets that indicate an event at the detector crystals 21 lying on the projection ray. During an emission scan, the coincidence counts are organized in memory 43, for example as a set of two-dimensional array, one for each axial image, and each having as one of its dimensions the projection angle θ and the other dimension the distance R. This θ by R map of the measured events may be referred to as sinogram array 48. The sorter 34 may also organize the coincidence events into other data formats. In a projection plane format, for example, other variables may be used to define coincidence events which are detected by pairs of detector crystals 21 in non-adjacent detector rings.

Coincidence events occur at random and the sorter 34 determines the θ and R values from the two crystal addresses in each coincidence data packet and increments the count of the corresponding sinogram array element. At the completion of the emission scan, the sinogram array 48 stores the total number of annihilation events which occurred along each ray. The array processor 45 reconstructs an image from the data in the sinogram array 48. First, however, a number of corrections may be made to the acquired data to correct for measurement errors such as those caused by attenuation of annihilation photons by the patient, detector gain non-uniformities, random coincidences, and integrator dead time. Each row of the corrected sinogram array is then Fourier transformed by the array processor 45 and multiplied by a one-dimensional filter array. The filtered data is then invers Fourier transformed, and each array element is back projected to form the image array 46. The image CPU 42 may either store the image array data or output the data to the operator work station 15. Alternatively, the image array 46 may be generated by an iterative image reconstruction algorithm run by the array processor 45 and/or the image CPU 42.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A system comprising:
   at least one detector configured to acquire imaging information;
   a processing unit operably coupled to the at least one detector and configured to acquire the imaging information from the at least one detector, the processing unit configured to:
      acquire patient scanning information for an imaging operation;
      determine a target activity using a model that is based on a relationship between activity level for a predetermined data quality metric and at least one parameter value of the patient scanning information;
      determine a target time for performing the imaging operation corresponding to the target activity;
      perform the imaging operation to acquire targeted imaging information at the target time; and
      reconstruct an image using the targeted imaging information.

2. The system of claim 1, wherein the at least one detector comprises at least one of a positron emission tomography (PET) detector or a computed tomography (CT) detector.

3. The system of claim 1, wherein the predetermined data quality metric is peak noise equivalent count (NEC).

4. The system of claim 1, wherein the relationship is a linear relationship between activity level for peak noise equivalent count (NEC) and patient weight.

5. The system of claim 1, further comprising a dose calibrator configured to determine a pre-injection activity level for a radiopharmaceutical to be administered, wherein the processing unit is configured to determine the target time using the pre-injection activity level and a decay characteristic for the radiopharmaceutical.

6. The system of claim 1, wherein the processing unit is configured to select a particular model to be used based on a type of scan specified by the patient scanning information.

7. The system of claim 1, wherein the imaging operation is performed in a series of frames, and the processing unit is configured to determine a frame target activity for at least some of the frames on a frame-by-frame basis.

8. The system of claim 7, wherein the processing unit is configured to determine an order for the frames to be imaged in based on the corresponding frame target activities.

9. A method comprising:
   acquiring, with at least one processor, patient scanning information for an imaging operation;
   determining, with the at least one processor, a target activity using a model that is based on a relationship between activity level for a predetermined data quality metric and at least one parameter value of the patient scanning information;
   determining a target time for performing the imaging operation corresponding to the target activity;
   performing the imaging operation to acquire targeted imaging information at the target time; and
   reconstructing an image using the targeted imaging information.

10. The method of claim 9, wherein the targeted imaging information is at least one of positron emission tomography (PET) imaging information or computed tomography (CT) imaging information.

11. The method of claim 9, wherein the predetermined data quality metric is a peak noise equivalent count (NEC).

12. The method of claim 9, wherein the relationship is a linear relationship between activity level for peak noise equivalent count (NEC) and patient weight.

13. The method of claim 9, further comprising determining, with a dose calibrator, a pre-injection activity level for a radiopharmaceutical to be administered, wherein the target time is determined using the pre-injection activity level and a decay characteristic for the radiopharmaceutical.

14. The method of claim 9, further comprising selecting a particular model to be used based on a type of scan specified by the patient scanning information.

15. The method of claim 9, wherein the imaging operation is performed in a series of frames, the method comprising determining a frame target activity for at least some of the frames on a frame-by-frame basis.

16. The method of claim 15, further comprising determining an order for the frames to be imaged in based on the corresponding frame target activities.

* * * * *